US007183087B2

(12) United States Patent
Lee et al.

(10) Patent No.: US 7,183,087 B2
(45) Date of Patent: Feb. 27, 2007

(54) PROCESS FOR PREPARING POLYHYDROXYALKANOATE EMPLOYING MAOC GENE

(75) Inventors: Sang Yup Lee, Daejeon (KR); Si Jae Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 164 days.

(21) Appl. No.: 10/662,358

(22) Filed: Sep. 16, 2003

(65) Prior Publication Data
US 2005/0037473 A1 Feb. 17, 2005

(30) Foreign Application Priority Data
Apr. 23, 2003 (KR) .................. 10-2003-0025863

(51) Int. Cl.
C12P 7/62 (2006.01)
C12N 1/20 (2006.01)
C12N 9/88 (2006.01)
C12N 15/00 (2006.01)
C07H 21/04 (2006.01)

(52) U.S. Cl. ................. 435/135; 435/252.33; 435/232; 435/320.1; 536/23.2

(58) Field of Classification Search ................ 435/232, 435/320.1, 252.33, 135; 536/23.2
See application file for complete search history.

(56) References Cited

U.S. PATENT DOCUMENTS
6,143,952 A 11/2000 Srienc et al.

FOREIGN PATENT DOCUMENTS
WO WO 98/54329 12/1998
WO WO 99/61624 12/1999
WO WO 01/55436 A1 8/2001

OTHER PUBLICATIONS

Ferrandez A. et al. Catabolism of Phenylacetic acid in *Escherichia coli*, J. Biol. Chem. 1998, 273, 25974-25986.*
Tsuge et al. Molecular cloning of two (R)-specific enoyl-CoA hydratase genes from *Pseudomonas aeruginosa* and their use for polyhydroxyalkanoate synthesis, FEMS Microbiology Letters, 1999, 189, 193-198.*
Agnihotri G. et al. Enoyl-CoA Hydratase: Reaction, Mechanism, and Inhibition, Bioorganic and Medicinal Chemistry, 2003, 11, 9-20.*
Park S. et al, Identiification and Characterization of a New Enoyl Coenzyme A Hydratase Involved in Biosynthesis of Medium—Chain—Length Polyhydroxyalkanoates in Recombinant *Escherichai coli*, J. Bacteriol. 2003, 185, 5391-5397.*
Park S. et al. Metabolic engineering of *Escherichia coli* for the production of medium-chain—length polyhydroxyalkanoates rich in specific monomers, FEMS Microbiology Letters, 2002, 214, 217-222.*

Fukui et al., "Expression and Characterization of (R)-Specific Enoyl Coenzyme A Hydratase Involved in Polyhydroxyalkanoate Biosynthesis by *Aeromonas caviae*," *Journal of Bacteriology*, vol. 180, No. 3, (Feb. 1998), pp. 667-673.
Tsuge et al., "Molecular cloning of two (R)-specific enoyl-CoA hydratase genes from *Pseudomonas aeruginosa* and their use for polyhydroxyalkanoate synthesis," *FEMS Microbiology Letters 184*, (1999), pp. 193-198.
Taguchi et al., "Co-expression of 3-ketoacyl-ACP reductase and polyhydroxyalkanoate synthase genes induced PHA production in *Escherichia coli* HB101 strain," *FEMS Microbiology Letters 176*, (1999), pp. 183-190.
Ren et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli*," *Journal of Bacteriology*, vol. 182, No. 10, (May 2000), pp. 2978-2981.
Park et al., "Metabolic engineering of *Escherichia coli* for the production of medium-chain-length polyhydroxyalkanoates rich in specific monomers," *FEMS Microbiology Letters 214*, (2002), pp. 217-222.
Qi et al., "Synthesis of poly(3-hydroxyalkanoates) in *Escherichia coli* expressing the PHA synthase gene phaC2 from *Pseudomonas aeruginosa*: comparison of PhaC1 and PhaC2," *FEMS Microbiology Letters 157*, (1997), pp. 155-162.
Qi et al., "Metabolic routing towards polyhydroxyalkanoic acid synthesis in recombinant *Escherichia coli (fadR)*: inhibition of fatty acid β-oxidation by acrylic acid," *FEMS Microbiology Letters 167*, (1998), pp. 89-94.
Langenbach et al., "Functional expression of the PHA synthase gene phaC1 from *Pseudomonas aeruginosa* in *Escherichia coli* results in poly(3-hydroxyalkanoate) synthesis," *FEMS Microbiology Letters 150*, (1997), pp. 303-309.
Snell et al., "YfcX Enables Medium-Chain-Length Poly(3-Hydroxyalkanoate) Formation from Fatty Acids in Recombinant *Escherichia coli fadB* Strains," *Journal of Bacteriology*, Oct. 2002, pp. 5696-5705.
Steinebach et al., "Cloning of the *maoA* gene that encodes aromatic amine oxidase of *Escherichia coli* W3350 and characterization of the overexpressed enzyme," *Eur. J. Biochem.*, vol. 237, (1996), pp. 584-591.

(Continued)

Primary Examiner—Rebecca Prouty
Assistant Examiner—Malgorzata Walicka
(74) Attorney, Agent, or Firm—Sughrue Mion, PLLC (57) ABSTRACT

The present invention relates to a method for producing middle-chain-length polyhydroxyalkanoate (MCL-PHA) using a maoC gene. The producing method of MCL-PHA according to the present invention comprises the steps of transforming a microorganism with the maoC gene to give a transformant, the microorganism being deleted of a fadB gene and containing a PHA synthase gene; culturing the transformant in medium containing a $C_{6-10}$ carbon source; and obtaining PHA consisting of monomers with 6–10 carbon atoms. When the maoC gene whose function has not yet been established is used according to the present invention, high quality PHA with a higher number of carbon atoms than the prior PHA can be produced at a higher efficiency.

7 Claims, 4 Drawing Sheets

OTHER PUBLICATIONS

Blattner et al., "The Complete Genome Sequence of *Escherichia coli* K-12," *Science*, vol. 277, (Sep. 5, 1997), pp. 1453-1462.

Jeong et al., "Excretion of Human β-Endorphin into Culture Medium by Using Outer Membrane Protein F as a Fusion Partner in Recombinant *Escherichia coli*," *Applied and Environmental Microbiology*, (vol. 68, No. 10, (Oct. 2002), pp. 4979-4985.

Park et al., "Enrichment of specific monomer in medium-chain-length poly(3-hydroxyalkanoates) by amplification of *fadD* and *fadE* genes in recombinant *Escherichia coli*," *Enzyme and Microbial Technology*, vol. 33, (2003), pp. 62-70.

Matsusaki et al., "Cloning and Molecular Analysis of the Poly(3-hydroxybutyrate) and Poly(3-hydroxybutyrate-*co*-3-hydroxyalkanoate) Biosynthesis Genes in *Pseudomonas* sp. Strain 61-3," *Journal of Bacteriology*, vol. 180, No. 24, (Dec. 1998), pp. 6459-6467.

Peekhaus et al., "Positive and Negative Transcriptional Regulation of the *Escherichia coli* Gluconate Regulation Gene *gntT* by GntR and the Cyclic AMP (cAMP)-cAMP Receptor Protein Complex," *Journal of Bacteriology*, vol. 180, No. 7, (Apr. 1998), pp. 1777-1785.

Sambrook et al., "Molecular Cloning, Second Edition, A Laboratory Manual," *Cold Spring Harbor Laboratory*, (1989), pp. xi-xxxv.

Kovach et al., "Four new derivatives of the broad-host-range cloning vestor pBBR1 MCS, carrying different antibiotic-resistance cassettes," *Gene*, vol. 166, (1995), pp. 175-176.

* cited by examiner

SEQUENCE LISTING

<160> NUMBER OF SEQ ID NOS: 11

<210> SEQ ID NO 1
<211> LENGTH: 681
<212> TYPE: PRT
<213> ORGANISM: Escherichia coli

<400> SEQUENCE: 1

```
Met Gln Gln Leu Ala Ser Phe Leu Ser Gly Thr Trp Gln Ser Gly Arg
1               5                   10                  15

Gly Arg Ser Arg Leu Ile His His Ala Ile Ser Gly Glu Ala Leu Trp
            20                  25                  30

Glu Val Thr Ser Glu Gly Leu Asp Met Ala Ala Arg Gln Phe Ala
        35                  40                  45

Ile Glu Lys Gly Ala Pro Ala Leu Arg Ala Met Thr Phe Ile Glu Arg
    50                  55                  60

Ala Ala Met Leu Lys Ala Val Ala Lys His Leu Leu Ser Glu Lys Glu
65                  70                  75                  80

Arg Phe Tyr Ala Leu Ser Ala Gln Thr Gly Ala Thr Arg Ala Asp Ser
                85                  90                  95

Trp Val Asp Ile Glu Gly Gly Ile Gly Thr Leu Phe Thr Tyr Ala Ser
            100                 105                 110

Leu Gly Ser Arg Glu Leu Pro Asp Asp Thr Leu Trp Pro Glu Asp Glu
        115                 120                 125

Leu Ile Pro Leu Ser Lys Glu Gly Gly Phe Ala Ala Arg His Leu Leu
    130                 135                 140

Thr Ser Lys Ser Gly Val Ala Val His Ile Asn Ala Phe Asn Phe Pro
145                 150                 155                 160

Cys Trp Gly Met Leu Glu Lys Leu Ala Pro Thr Trp Leu Gly Gly Met
                165                 170                 175

Pro Ala Ile Ile Lys Pro Ala Thr Ala Thr Ala Gln Leu Thr Gln Ala
            180                 185                 190

Met Val Lys Ser Ile Val Asp Ser Gly Leu Val Pro Glu Gly Ala Ile
        195                 200                 205

Ser Leu Ile Cys Gly Ser Ala Gly Asp Leu Leu Asp His Leu Asp Ser
    210                 215                 220

Gln Asp Val Val Thr Phe Thr Gly Ser Ala Ala Thr Gly Gln Met Leu
225                 230                 235                 240

Arg Val Gln Pro Asn Ile Val Ala Lys Ser Ile Pro Phe Thr Met Glu
                245                 250                 255

Ala Asp Ser Leu Asn Cys Cys Val Leu Gly Glu Asp Val Thr Pro Asp
            260                 265                 270

Gln Pro Glu Phe Ala Leu Phe Ile Arg Glu Val Val Arg Glu Met Thr
        275                 280                 285

Thr Lys Ala Gly Gln Lys Cys Thr Ala Ile Arg Arg Ile Ile Val Pro
    290                 295                 300
```

-continued

```
Gln Ala Leu Val Asn Ala Val Ser Asp Ala Leu Val Ala Arg Leu Gln
305                 310                 315                 320

Lys Val Val Val Gly Asp Pro Ala Gln Glu Gly Val Lys Met Gly Ala
                325                 330                 335

Leu Val Asn Ala Glu Gln Arg Ala Asp Val Gln Glu Lys Val Asn Ile
            340                 345                 350

Leu Leu Ala Ala Gly Cys Glu Ile Arg Leu Gly Gly Gln Ala Asp Leu
        355                 360                 365

Ser Ala Ala Gly Ala Phe Phe Pro Pro Thr Leu Leu Tyr Cys Pro Gln
    370                 375                 380

Pro Asp Glu Thr Pro Ala Val His Ala Thr Glu Ala Phe Gly Pro Val
385                 390                 395                 400

Ala Thr Leu Met Pro Ala Gln Asn Gln Arg His Ala Leu Gln Leu Ala
                405                 410                 415

Cys Ala Gly Gly Gly Ser Leu Ala Gly Thr Leu Val Thr Ala Asp Pro
            420                 425                 430

Gln Ile Ala Arg Gln Phe Ile Ala Asp Ala Ala Arg Thr His Gly Arg
        435                 440                 445

Ile Gln Ile Leu Asn Glu Glu Ser Ala Lys Glu Ser Thr Gly His Gly
    450                 455                 460

Ser Pro Leu Pro Gln Leu Val His Gly Pro Gly Arg Ala Gly Gly
465                 470                 475                 480

Gly Glu Glu Leu Gly Gly Leu Arg Ala Val Lys His Tyr Met Gln Arg
                485                 490                 495

Thr Ala Val Gln Gly Ser Pro Thr Met Leu Ala Ala Ile Ser Lys Gln
            500                 505                 510

Trp Val Arg Gly Ala Lys Val Glu Glu Asp Arg Ile His Pro Phe Arg
        515                 520                 525

Lys Tyr Phe Glu Glu Leu Gln Pro Gly Asp Ser Leu Leu Thr Pro Arg
    530                 535                 540

Arg Thr Met Thr Glu Ala Asp Ile Val Asn Phe Ala Cys Leu Ser Gly
545                 550                 555                 560

Asp His Phe Tyr Ala His Met Asp Lys Ile Ala Ala Glu Ser Ile
                565                 570                 575

Phe Gly Glu Arg Val Val His Gly Tyr Phe Val Leu Ser Ala Ala Ala
            580                 585                 590

Gly Leu Phe Val Asp Ala Gly Val Gly Pro Val Ile Ala Asn Tyr Gly
        595                 600                 605

Leu Glu Ser Leu Arg Phe Ile Glu Pro Val Lys Pro Gly Asp Thr Ile
    610                 615                 620

Gln Val Arg Leu Thr Cys Lys Arg Lys Thr Leu Lys Lys Gln Arg Ser
625                 630                 635                 640

Ala Glu Glu Lys Pro Thr Gly Val Val Glu Trp Ala Val Glu Val Phe
                645                 650                 655

Asn Gln His Gln Thr Pro Val Ala Leu Tyr Ser Ile Leu Thr Leu Val
            660                 665                 670

Ala Arg Gln His Gly Asp Phe Val Asp
        675                 680
```

<210> SEQ ID NO 2
<211> LENGTH: 2046
<212> TYPE: DNA
<213> ORGANISM: Escherichia coli

<400> SEQUENCE: 2

-continued

```
atgcagcagt tagccagttt cttatccggt acctggcagt ctggccgggg ccgtagccgt      60
ttgattcacc acgctattag cggcgaggcg ttatgggaag tgaccagtga aggtcttgat     120
atggcggctg cccgccagtt tgccattgaa aaaggtgccc ccgcccttcg cgctatgacc     180
tttatcgaac gtgcggcgat gcttaaagcg gtcgctaaac atctgctgag tgaaaaagag     240
cgtttctatg ctctttctgc gcaaacaggc gcaacgcggg cagacagttg ggttgatatt     300
gaaggtggca ttgggacgtt atttacttac gccagcctcg gtagccggga gctgcctgac     360
gatacgctgt ggccggaaga tgaattgatc cccttatcga agaaggtgg atttgccgcg      420
cgccatttac tgacctcaaa gtcaggcgtg gcagtgcata ttaacgcctt taacttcccc     480
tgctggggaa tgctggaaaa gctggcacca acgtggctgg cggaatgcc agccatcatc      540
aaaccagcta ccgcgacggc ccaactgact caggcgatgg tgaaatcaat tgtcgatagt     600
ggtcttgttc ccgaaggcgc aattagtctg atctgcggta gtgctggcga cttgttggat     660
catctggaca gccaggatgt ggtgactttc acggggtcag cggcgaccgg acagatgctg     720
cgagttcagc caaatatcgt cgccaaatct atccccttca ctatggaagc tgattccctg     780
aactgctgcg tactgggcga agatgtcacc ccggatcaac cggagtttgc gctgtttatt     840
cgtgaagttg tgcgtgagat gaccacaaaa gccgggcaaa aatgtacggc aatccggcgg     900
attattgtgc cgcaggcatt ggttaatgct gtcagtgatg ctctggttgc gcgattacag     960
aaagtcgtgg tcggtgatcc tgctcaggaa ggcgtgaaaa tgggcgcact ggtaaatgct    1020
gagcagcgtg ccgatgtgca ggaaaaagtg aacatattgc tggctgcagg atgcgagatt    1080
cgcctcggtg gtcaggcgga tttatctgct gcgggtgcct tcttcccgcc aaccttattg    1140
tactgtccgc agccggatga acaccggcg gtacatgcaa cagaagcctt tggccctgtc     1200
gcaacgctga tgccagcaca aaaccagcga catgctctgc aactggcttg tgcaggcggc    1260
ggtagccttg cgggaacgct ggtgacggct gatccgcaaa ttgcgcgtca gtttattgcc    1320
gacgcggcac gtacgcatgg gcgaattcag atcctcaatg aagagtcggc aaaagaatcc    1380
accgggcatg gctccccact gccacaactg gtacatggtg ggcctggtcg cgcaggaggc    1440
ggtgaagaat taggcggttt acgagcggtg aaacattaca tgcagcgaac cgctgttcag    1500
ggtagtccga cgatgcttgc cgctatcagt aaacagtggg tgcgcggtgc gaaagtcgaa    1560
gaagatcgta ttcatccgtt ccgcaaatat tttgaggagc tacaaccagg cgacagcctg    1620
ttgactcccc gccgcacaat gacagaggcc gatattgtta actttgcttg cctcagcggc    1680
gatcatttct atgcacatat ggataagatt gctgctgccg aatctatttt cggtgagcgg    1740
gtggtgcatg gtattttgt gctttctgcg gctgcgggtc tgtttgtcga tgccggtgtc     1800
ggtccggtca ttgctaacta cgggctggaa agcttgcgtt ttatcgaacc cgtaaagcca    1860
ggcgatacca tccaggtgcg tctcacctgt aagcgcaaga cgctgaaaaa acagcgtagc    1920
gcagaagaaa aaccaacagg tgtggtggaa tgggctgtag aggtattcaa tcagcatcaa    1980
accccggtgg cgctgtattc aattctgacg ctggtggcca ggcagcacgg tgatttttgtc   2040
gattaa                                                               2046
```

<210> SEQ ID NO 3
<211> LENGTH: 80
<212> TYPE: DNA
<213> ORGANISM: Artificial Sequence
<220> FEATURE:
<223> OTHER INFORMATION: PCR primer

```
<400> SEQUENCE: 3
atgcagcagt tagccagttt cttatccggt acctggcagt ctggccgggg ccgtagccgt    60
agcacttcac tgacaccctc                                                80

<210> SEQ ID NO 4
<211> LENGTH: 71
<212> TYPE: DNA
<213> ORGANISM: Artificial Sequence
<220> FEATURE:
<223> OTHER INFORMATION: PCR primer

<400> SEQUENCE: 4
ttaatcgaca aaatcaccgt gctgcctggc caccagcgtc agaattgaat aacttattca    60
ggcgtagcac c                                                         71

<210> SEQ ID NO 5
<211> LENGTH: 47
<212> TYPE: DNA
<213> ORGANISM: Artificial Sequence
<220> FEATURE:
<223> OTHER INFORMATION: PCR primer

<400> SEQUENCE: 5
cgcggatcca ataaggagat atctagatga gagagaaacc aacgccg                  47

<210> SEQ ID NO 6
<211> LENGTH: 50
<212> TYPE: DNA
<213> ORGANISM: Artificial Sequence
<220> FEATURE:
<223> OTHER INFORMATION: PCR primer

<400> SEQUENCE: 6
cggatccccg ggtaccgagc tcgaattctc agcgcacgcg cacgtaggta              50

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
gactagttga aggtgtgcg cgatctcac                                       29

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8
gcggatccca tttgttatgg gcgacgtcaa ttt                                 33

<210> SEQ ID NO 9
<211> LENGTH: 31
<212> TYPE: DNA
<213> ORGANISM: Artificial Sequence
<220> FEATURE:
<223> OTHER INFORMATION: PCR primer

<400> SEQUENCE: 9
tttcccgagc tcatgcagca gttagccagt t                                   31
```

```
<210> SEQ ID NO 10
<211> LENGTH: 28
<212> TYPE: DNA
<213> ORGANISM: Artificial Sequence
<220> FEATURE:
<223> OTHER INFORMATION: PCR primer

<400> SEQUENCE: 10
gctctagatt aatcgacaaa atcaccgt                                            28

<210> SEQ ID NO 11
<211> LENGTH: 45
<212> TYPE: DNA
<213> ORGANISM: Artificial Sequence
<220> FEATURE:
<223> OTHER INFORMATION: PCR primer

<400> SEQUENCE: 11
gctctagatt aatggtgatg atggtgatga tcgacaaaat caccg                         45
```

PROCESS FOR PREPARING POLYHYDROXYALKANOATE EMPLOYING *MAOC* GENE

Priority is claimed to Korean patent application number 10-2003-0025863, filed Apr. 23, 2003.

The present invention relates to a method for producing polyhydroxyalkanoate (hereinafter, referred to as "PHA") using a maoC gene. More particularly, the present invention relates to a maoC gene, a MaoC protein having enoyl-CoA hydratase activity, and a method for producing PHA using a microorganism transformed with a recombinant vector containing the maoC gene and a recombinant vector containing a PHA synthase gene.

BACKGROUND ART

PHA is a polyester-type compound which accumulates within a microorganism as a carbon source when the microorganism has excess sources of carbon available with a corresponding lack of nutrients, such as phosphorus, nitrogen, magnesium and oxygen. Since this PHA has physical properties similar to synthetic polymers originated from petroleum, while showing complete biodegradability, it is being recognized as a substitute for prior synthetic plastics.

Generally, PHA is divided into short-chain-length PHA (SCL-PHA) with a small number of carbon atoms and medium-chain-length PHA (MCL-PHA) with a relatively large number of carbon atoms. Since MCL-PHA has more similar physical properties to synthetic polymer than SCL-PHA, studies on generally MCL-PHA are being actively conducted. To produce PHA in a microorganism, different enzymes are required: enzymes capable of converting metabolites of the microorganism into PHA monomers, and a PHA synthase capable of synthesizing a PHA polymer from the PHA monomers. The enzymes known to provide the PHA monomers include (R)-specific enoyl-CoA hydratase found in *Aeromonas* sp. microorganisms and *Pseudomonas* sp. microorganisms, and 3-ketoacyl-ACP reductase found in *E. coli* and *Pseudomonas* sp. microorganisms (Fukui et al., *J. Bacteriol.*, 180:667–73, 1998; Tsuge et al., *FEMS Microbiol. Lett.*, 184: 193–8, 2000; Taguchi et al., *FEMS Microbiol. Lett.*, 176: 183–90, 1999; Ren et al., *J. Bacteriol.*, 182:2978–81, 2000; and Park et al., *FEMS Microbiol. Lett.*, 214:217–22, 2002).

Meanwhile, it was reported that a MCL-PHA synthase gene was cloned from a *Pseudomonas* sp. microorganism, and MCL-PHA could be synthesized using a recombinant microorganism transformed with this gene (Qi et al., *FEMS Microbiol. Lett.*, 157:155–62, 1997; Qi et al., *FEMS Microbiol. Lett.*, 167:89–94, 1998; Langenbach et al., *FEMS Microbiol. Lett.*, 150:303–9, 1997; WO 01/55436; U.S. Pat. No. 6,143,952; WO 98/54329; and WO 99/61624). Furthermore, it was reported that the use of a recombinant *E. coli*, from which FadB among enzymes of fatty acid degradation pathway had been deleted, could also produce MCL-PHA (Langenbach et al., *FEMS Microbiol. Lett.*, 150:303–9, 1997).

On the other hand, since it was reported that YfcX enzyme, homologous to FadB could provide the PHA monomers when the fadB gene-deleted recombinant *E. coli* was used (Snell et al., *J. Bacteriol.*, 184: 5696–5705, 2002) it was predicted that new enzymes of providing the PHA monomers besides YfcX would exist. Because the use of the fadB gene-deleted recombinant *E. coli* can effectively produce MCL-PHA, efforts to discover the enzymes of providing the PHA monomers in the fadB gene-deleted recombinant *E. coli* were continued but there were no particular results up to now.

Accordingly, there was a continued need to discover the new enzymes of providing the PHA monomers in *E. coli*.

DISCLOSURE OF INVENTION

Therefore, the present inventors have conducted extensive studies to discover a new enzyme of providing PHA monomers in *E. coli*, and consequently, found that a protein expressed from an *E. coli* gene maoC whose other functions had not been yet established, could serve as the enzyme of providing the PHA monomers in fadB gene-deleted recombinant *E. coli*. On the basis of this point, the present invention was perfected.

An object of the present invention is to provide a maoC gene, a MaoC protein, a recombinant vector containing the maoC gene, and a microorganism transformed with the recombinant vector.

Another object of the present invention is to provide a method for producing medium-chain-length PHA using the maoC gene.

To achieve the above objects, in one aspect, the present invention provides a maoC gene coding for a MaoC protein represented by SEQ ID NO: 1.

In another aspect, the present invention provides a maoC gene, which has a DNA sequence of SEQ ID NO: 2 and codes for a protein of providing monomers necessary for MCL-PHA synthesis.

In yet another aspect, the present invention provides a recombinant vector containing the maoC gene.

In still another aspect, the present invention provides a MaoC protein, which has an amino acid sequence of SEQ ID NO: 1 and shows enoyl-CoA hydratase activity.

In further another aspect, the present invention provides a microorganism transformed with the recombinant vector.

In the present invention, the microorganism is preferably deleted of a fadB gene and contains a PHA synthase gene. Also, the microorganism is preferably transformed with a recombinant vector containing the PHA synthase gene, or has the PHA synthase gene inserted into a chromosome.

In the present invention, the PHA synthase gene is preferably phaC.

In another aspect, the present invention provides a method for producing middle-chain-length PHA (MCL-PHA), which comprises the steps of: culturing the transformed microorganism in a medium containing a $C_{6-10}$ carbon source; and obtaining MCL-PHA consisting of monomers with 6–10 carbon atoms.

Furthermore, the present invention provides MCL-PHA, which is produced as described above so that the content of each of 3-hydroxyoctanoate (3HO) and 3-hydroxydecanoate (3HD) in the total monomers of MCL-PHA is more than 30%.

Tsuge et al. reported enoyl-CoA hydratase involved in the synthesis of PHA in *Pseudomonas* sp. (Tsuge et al., *FEMS Microbiol. Lett.*, 184:193–8, 2000). To discover a new enzyme of providing PHA monomers in *E. coli*, the present inventors searched for proteins, which are expressed in *E. coli* and have an amino acid sequence showing high homology with that of the reported enoyl-CoA hydratase. As a result, a MaoC protein of SEQ ID NO: 1 showing a homology of 34%, and a gene of SEQ ID NO: 2 coding for this protein, were discovered. Up till now the exact function of the MaoC protein was not established, and only the fact that each of maoC and maoA genes consists of one operon was reported (Steinebach et al., *Eur. J. Biochem.*, 237: 584–91, 1996).

The present inventors predicted that the discovered protein would show enoyl-CoA hydratase activity involved in PHA synthesis. To confirm this, the maoC gene coding for the MaoC protein was cloned. In other words, using the *E. coli* chromosome as a template, a maoC$_{Ec}$ gene was amplified by PCR using an oligonucleotide primer synthesized on the basis of the genomic sequence of *E. coli* (Blattner et al., *Science* 277:1453–62, 1997). The amplified maoC$_{Ec}$ gene was digested with SacI/XbaI and cloned into a p10499A recombinant vector, thereby constructing a p10499MaoC vector. A gene fragment obtained by digesting the p10499MaoC vector with EcoRV/ScaI was inserted into pACYC184 digested with PvuII/DraI, thereby constructing a pACYC104MaoC recombinant vector for expressing the maoC gene.

A p10499613C2 vector capable of expressing the PHA synthase gene was digested with EcoRV/SspI, and inserted into pBBR1MCS digested with EcoRV, thereby constructing a pMCS 104613C2 recombinant vector containing the PHA synthase gene.

According to the method of Jeong and Lee, a maoC gene was deleted from mutant *E. coli* WB101 from which a fadB gene had been deleted, thereby producing mutant *E. coli* WB106 from which both the fadB and maoC genes had been deleted (Jeong and Lee., *Appl. Environ. Microbiol.*, 68:4979–85, 2002).

The mutant *E. coli* WB101 from which only the fabB gene had been deleted could produce MCL-PHA from decanoate with 10 carbon atoms even when it was transformed with pMCS104613C2 containing the PHA synthase gene, but the mutant *E. coli* WB106 from which both the fadB and maoC genes had been deleted could not produce MCL-PHA from decanoate with 10 carbon atoms when it was transformed with only pMCS104613C2. However, *E. coli* W3110 obtained by the transformation of *E. coli* WB106 with both pMCS 104613C2 and pACYC104MaoC could produce MCL-PHA from decanoate with 10 carbon atoms.

Although medium for use in culturing of *E. coli* is not specially limited, it is preferred to use Luria-Bertani (LB) medium (yeast extract 5 g/L, peptone 10 g/L, NaCl 5 g/L), which is generally used in culturing of *E. coli*. It could be found that PHA produced according to the present invention showed superior yield to PHA produced by the prior method, and contained 3-hydroxyhexanoate (3HHx), 3-hydroxyoctanoate (3HO) and 3-hydroxydecanoate (3HD) as monomers, and particularly 3HO and 3HD formed most of the monomers. Thus, it was found that PHA produced by the present invention has superior quality to PHA produced by the prior method.

To measure the enzyme activity of the protein expressed from the maoC gene, recombinant vector pTac99MaoCH expressing the MaoC protein labeled with 6 histidines was constructed, and MaoC-His$_6$-Tag was obtained using the recombinant vector pTac99MaoCH. This MaoC-His$_6$-Tag showed an enoyl-CoA hydratase activity of 47.6 U/mg as measured in the presence of crotonyl-CoA as a substrate. As used herein, "1U" is defined as a unit of enzyme activity for removing 1 µmol of crotonyl-CoA per minute.

BEST DETAILED DESCRIPTION OF THE INVENTION

The present invention will hereinafter be described in further detail by examples. It will however be obvious to a person skilled in the art that these examples are given for illustrative purpose only, and the scope of the present invention is not limited to or by these examples.

EXAMPLE 1

Production of Recombinant *E. coli* for Producing PHA Using maoC Gene

Mutant *E. coli* from which fadB and maoC genes had been deleted, a recombinant vector containing an *E. coli* maoC gene, and a recombinant vector containing a MCL-PHA synthase gene, were constructed. Using each of these recombinant vectors, recombinant *E. coli* for use in the production of MCL-PHA was produced.

EXAMPLE 1-1

Production of Mutant *E. coli* from which fadB and maoC Genes had Been Deleted

According to the conventional method, a maoC gene was deleted from *E. coli* using the red operon of bacteriophage λ (Jeong and Lee, *Appl. Environ. Microbiol.*, 68:4979–85, 2002).

In other words, mutant *E. coli* WB101 from which a fadB gene had been deleted was transformed with vector pTrcEBG (Jeong and Lee, *Appl. Environ. Microbiol.*, 68:4979–85, 2002) containing the red operon of bacteriophage λ, and added with 1 mM IPTG to induce the expression of red operon in the *E. coli*. WB101 transformed with pTrcEBG, and a electroporation-competent cell was produced using this *E. coli*. The *E. coli* WB101 was produced by deleting the fadB gene from *E. coli* W3110 (ATCC 39936) (Park et al., *Enzyme Micro. Technol.*, 33: 62–70, 2003).

Meanwhile, since 60 bp from the 5' end and 60 bp from the 3' end of the maoC gene contain DNA sequences similar to 60 bp from the 5' end and 60 bp from the 3' end of a chloromphenicol-resistant gene, the substitution of the maoC gene with the chloromphenicol-resistant gene can produce a maoC gene-deleted mutant. For this purpose, using pACYC184 (New England Biolab, USA) as a template and primers MaoCdelf (SEQ ID NO: 3) and MaoCdelb (SEQ ID NO: 4), 30 cycles of PCR consisting of denaturation at 94° C. for 50 seconds, annealing at 52° C. for 50 seconds and extension at 72° C. for one minute was carried out, thereby producing a PCR fragment.

```
5'-atgcagcagttagccagtttcttatccggtac   (SEQ ID NO: 3)
ctggcagtctggccgggcgtagccgtagcactt
cactgacaccctc-3'
```

-continued

5'-ttaatcgacaaaatcaccgtgctgcctggcca    (SEQ ID NO: 4)

ccagcgtcagaatt gaataacttattcaggcgta gcacc-3'

The PCR fragment was cloned into the electroporation-competent cell produced as described above, thereby constructing mutant E. coli WB106 from which both the fadB and maoC genes had been deleted.

EXAMPLE 1-2

Construction of p10499A and p10499613C2

Using the chromosomal DNA of Pseudomonas sp. 61–3 (JCM 10015) containing a PHA synthase gene (Matsusaki et al., J. Bacteriol., 180: 6459–67, 1998) as a template and primers phaC2$_{Ps}$-1 (SEQ ID NO: 5) and phaC2$_{Ps}$-2 (SEQ ID NO: 6), 30 cycles of PCR consisting of denaturation at 94° C. for 50 seconds, annealing at 52° C. for 50 seconds and extension at 72° C. for 2 minutes was carried out, thereby producing a PCR product.

5'-cgcggatccaataaggagatatctagatgaga    (SEQ ID NO: 5)

gagaaaccaacgccg-3'

5'-cggatccccgggtaccgagctcgaattctcag    (SEQ ID NO: 6)

cgcacgcgcacgtaggta-3'

The analysis of the PCR product was conducted by agarose gel electrophoresis and showed a 1.7 kb gene fragment corresponding to a phaC2Ps gene.

Moreover, to amplify a gntT104 promoter such that the PHA synthase gene is continued to express, 30 cycles of PCR consisting of denaturation at 94° C. for 50 seconds, annealing at 52° C. for 50 seconds and extension at 72° C. for 2 minutes was conducted using the chromosomal gene of E. coli W3110 (ATCC 39936) as a template and primers gntT104-1 (SEQ ID NO: 7) and gntT104-2 (SEQ ID NO: 8) (Peekhaus and Conway, J. Bacteriol., 180:1777–85, 1998).

5'-gactagttgaaaggtgtgcgcgatctcac-3'    (SEQ ID NO: 7)

5'-gcggatcccatttgttatgggcgacgtcaatt    (SEQ ID NO: 8)

t-3'

The analysis of the PCR product was conducted by agarose gel electrophoresis and showed a 400 bp gene fragment.

Plasmid pTrc99A (Pharmacia Biotech. Co., Uppsala, Sweden) was digested with EcoRV/EcoRI, and then, a gntT104 promoter gene fragment digested with the same enzymes was ligated to the pTrc99A plasmid by T4 DNA ligase, thereby a p10499A vector (Park et al., FEMS Microbiol. Lett., 214: 217–22, 2002). Then, the p10499A vector was digested with EcoRI/HindIII, after which the amplified phaC2$_{Ps}$ gene was inserted into EcoRI/HindIII recognition sites of the p10499A vector, thereby constructing recombinant expression vector p10499613C2.

EXAMPLE 1-3

Construction of Recombinant Vector Containing maoC Gene

First, the chromosomal DNA of E. coli W3110 was isolated and purified according to a known method (Sambrook et al., Molecular cloning, 2nd ed, Cold Spring Harbor Laboratory Press, NY, 1989). Using the purified E. coli genomic sequence as a template, and primers maoC 1 (SEQ ID NO: 9) and maoC 2 (SEQ ID NO: 10), 30 cycles of PCR consisting of denaturation at 94° C. for 50 seconds, annealing at 52° C. for 50 seconds and extension at 72° C. for 2 minutes was conducted, thereby giving a PCR fragment.

5'-tttcccgagctcatgcagcagtt    (SEQ ID NO: 9)

agccagtt-3'

5'-gctctagattaatcgacaaaatc    (SEQ ID NO: 10)

accgt-3'

Figure 1:
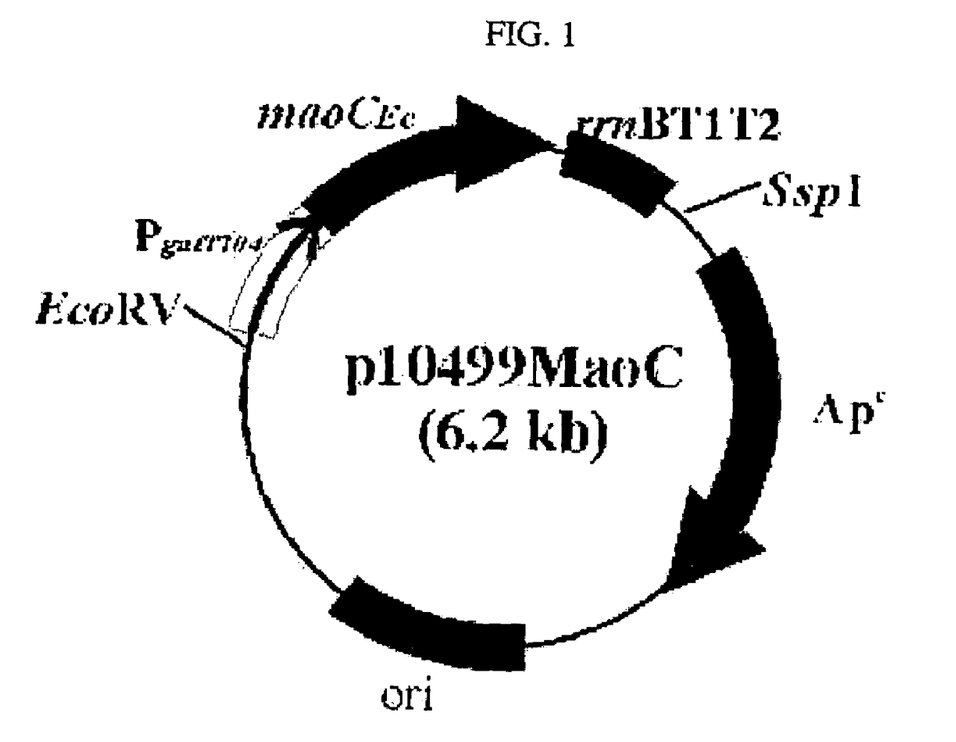
FIG. 1 is a gene map of recombinant vector p10499MaoC containing a maoC gene.
Figure 2:
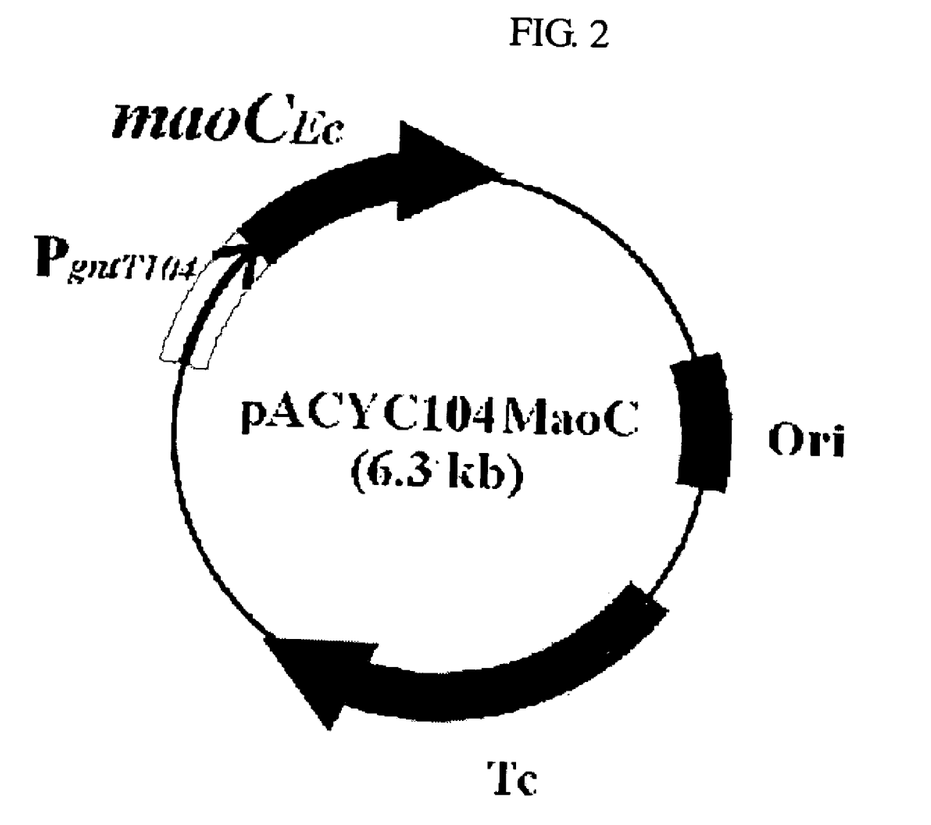
FIG. 2 is a gene map of recombinant vector pACYC104MaoC containing a maoC gene.

Meanwhile, the p10499A vector was digested with SacI/XbaI and then inserted with the PCR fragment, thereby constructing recombinant vector p10499MaoC. The p10499MaoC recombinant vector was digested with EcoRV/ScaI, cloned into pACYC184 digested with PvuII/DraI, thereby constructing recombinant vector pACYC104MaoC (see, FIGS. 1 and 2). FIG. 1 is a gene map of the recombinant vector p10499MaoC containing the maoC gene, and FIG. 2 is a gene map of the recombinant vector pACYC104MaoC containing the maoC gene.

EXAMPLE 1-4

Construction of Recombinant Vector Containing MCL-PHA Synthase Gene

Figure 3:
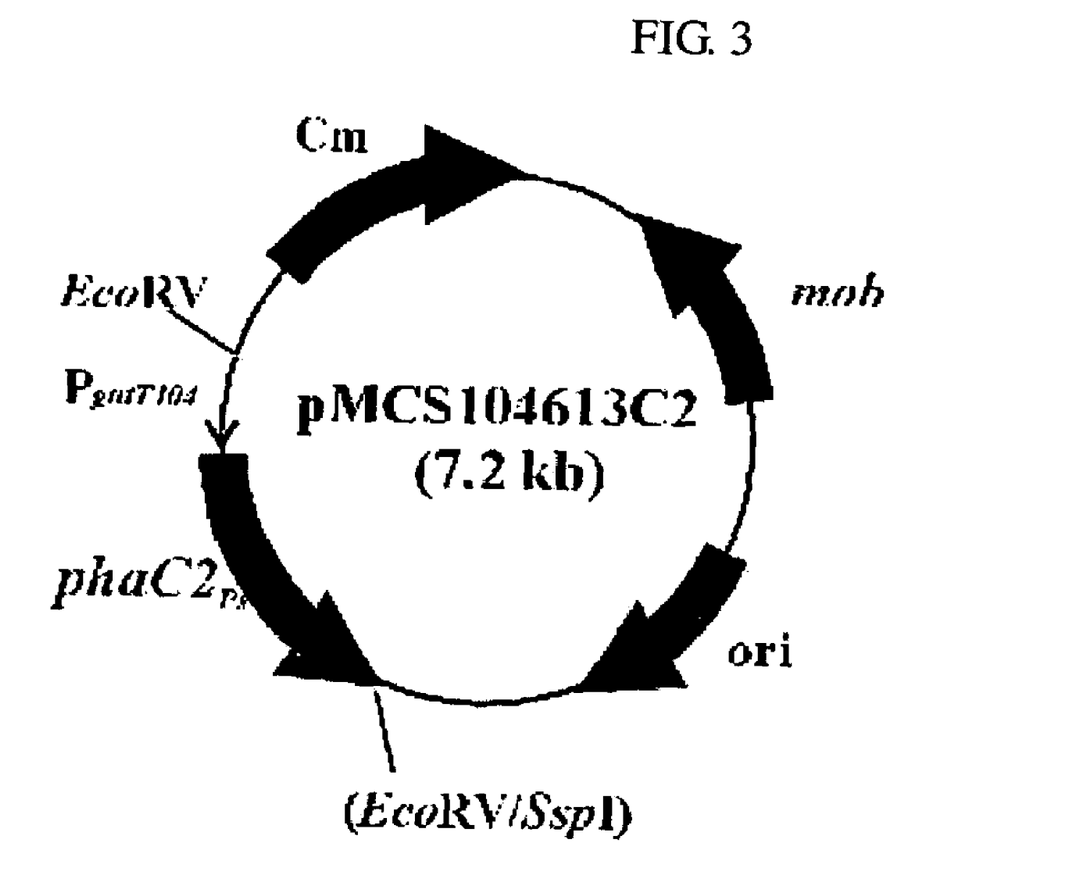
FIG. 3 is a gene map of recombinant vector pMCS104613C2 containing a PHA synthase gene.

For expression of a MCL-PHA synthase gene, a gene fragment obtained by digesting p10499613C2 with EcoRV/SspI was cloned into pBBR1MCS (Kovach et al., Gene, 166: 175–6, 1995) digested with EcoRV, thereby constructing MCL-PHA synthase gene recombinant vector pMCS104613C2 (see, FIG. 3). FIG. 3 is a gene map of the recombinant vector pMCS104613C2 containing the PHA synthase gene.

EXAMPLE 1-5

Production of Recombinant E. coli

The mutant E. coli WB101 from which the fadB gene had been deleted, and the mutant E. coli WB 106 from which both the fadB and maoC genes had been deleted, were transformed with the MCL-PHA synthase gene recombinant vector pMCS104613C2 and the MaoC recombinant vector p10499MaoC, and the MaoC recombinant vector pACYC104MaoC, thereby producing recombinant E. coli strains WB101 (transformed with pMCS 104613C2), WB101 (transformed with pMCS 104613C2+p10499MaoC), WB106 (transformed with pMCS104613C2) and WB106 (transformed with pMCS104613C2+pACYC104MaoC). As a control group, recombinant E. coli W3110 was used, which had been produced by transformation of normal E. coli W3110 with the PHA synthase gene recombinant vector pMCS104613C2 and the MaoC expression recombinant vector p 10499MaoC.

EXAMPLE 2

Measurement of MCL-PHA-Synthesizing Capability of Recombinant E. coli

In order to measure the MCL-PHA-synthesizing capability of the control group *E. coli* strain, and the test group *E. coli* strains WB101 (pMCS104613C2), WB101 (pMCS104613C2+p10499MaoC), WB106 (pMCS104613C2) and WB106 (pMCS104613C2+ pACYC104MaoC) produced in Example 1-5, each of the recombinant *E. coli* strains was cultured in LB medium (yeast extract 5 g/L, peptone 10 g/L, NaCl 5 g/L) containing 2 g/l of decanoate for 4 days. Then, the culture broth was centrifuged at 2,500 rpm for 15 minutes, and dried at 100° C. According to the conventional method, MCL-PHA was isolated from the dried colony and measured for its content in the colony.

In order to measure the composition of the isolated MCL-PHA, the isolated MCL-PHA was subjected to methanolysis to convert it into the form of 3-hydroxyalkanoic acid methyl ester, and the composition ratio between 3-hydroxybutyrate (3HB), 3-hydroxyhexanoate (3HHx), 3-hydroxyoctanoate (3HO), 3-hydroxydecanoate (3HD) and 3-hydroxydodecanoate (3HDD) was measured by gas chromatography (Donan Co., Korea). In this case, a fused silica capillary column (Supelco SPBTM-5, 30m 0.32 mm ID 0.25m film, USA) was used as a GC column, and benzoic acid (Sigma Chem. Co., USA) was used as the internal standard. The measured results are given in Table 1 below.

TABLE 1

Content and composition ratio of MCL-PHA in recombinant *E. coli*.

| Test group | MCL-PHA content (%, w/w) | Composition ratio (mol %) | | | | |
|---|---|---|---|---|---|---|
| | | 3HB | 3HHx | 3HO | 3HD | 3HHD |
| Control | 11.9 | 0 | 19 | 74 | 7 | 0 |
| WB101 (pMCS104613C2) | 44.6 | 0 | 9 | 37 | 54 | 0 |
| WB101 (pMCS104613C2 + p10499MaoC) | 20.0 | 0 | 0 | 61 | 39 | 0 |
| WB106 (pMCS104613C2) | 0 | 0 | 0 | 0 | 0 | 0 |
| WB106 (pMCS104613C2 + pACYC104MaoC) | 10 | 0 | 12 | 38 | 49 | 0 |

As evident from Table 1 above, MCL-PHA was produced in the control group *E. coli* strain, and the test group *E. coli* strains WB101 (pMCS104613C2) and WB101 (pMCS104613C2+p10499MaoC), but not produced in the *E. coli* strains WB106 (pMCS104613C2) from which the maoC gene had been deleted. However, since MCL-PHA was produced in the recombinant *E. coli* WB106 (pMCS104613C2+pACYC104MaoC) where the maoC gene was cloned into the maoC gene-deleted recombinant *E. coli*, it could be found that the maoC gene played an important role in the production of MCL-PHA.

Langenbach et al. reported that MCL-PHA was produced in a fadB mutant *E. coli* strain transformed with recombinant vector pBHR71 containing a phaC1$_{Pa}$ gene, at a content of 21.1%(w/w) of cell dry weight (Langenbach et al., *FEMS Microbiol. Lett.*, 150:303–9, 1997). Tsuge et al. reported that MCL-PHA was produced in a recombinant *E. coli* strain expressing the PHA synthase gene originated from *Pseudomonas* sp. and the (R)-specific enoyl-CoA hydratases PhaJ1 and PhaJ2 originated from *Pseudomonas* sp., at contents of 14 and 29% (w/w) of cell dry weight, and the produced PHA mainly consisted of monomers with 6 carbon atoms (Tsuge et al., *FEMS Microbiol. Lett.*, 184:193–8, 2000).

In comparison with this prior art, the present invention allowed MCL-PGA to be produced at a higher content (44.6% (w/w)) than the prior art (14, 21.1 and 29%(w/w)). Furthermore, MCL-PHA produced according to the prior art consisted mainly of monomers with 6 carbon atoms, whereas MCL-PHA produced according to the method of the present invention consisted of monomers with 6–10 carbon atoms (3HHx, 3HO and 3HD), and particularly contained a large amount of monomers with 8–10 carbon atoms (3HO and 3HD). Thus, it could be found that MCL-PHA produced according to the method of the present invention would be used in a significantly wide range of application fields as compared to PHA produced by the prior method.

EXAMPLE 3

Measurement of enoyl-CoA Hydratase Activity

Figure 4:
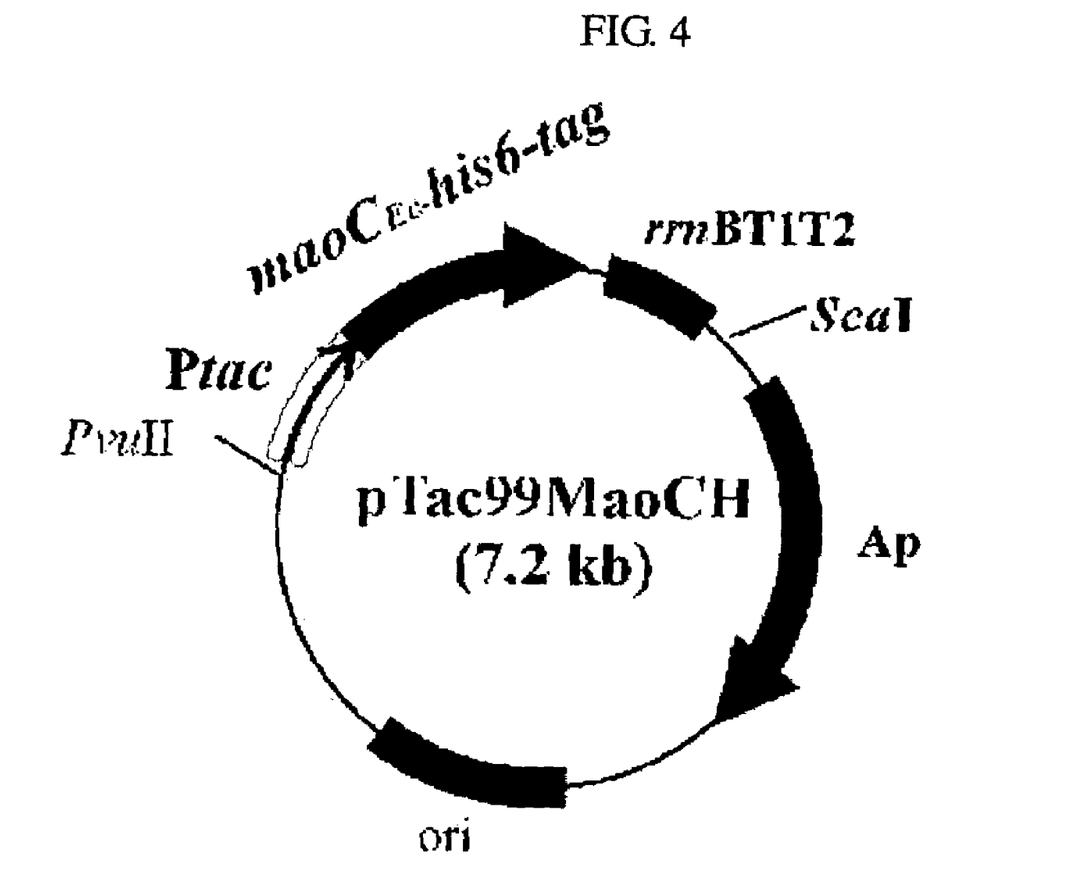
FIG. 4 is a gene map of recombinant vector pTac99MaoCH containing a maoC gene.

A PCR fragment was produced in the same manner as Example 1-2 except that primer His-Tag: 5'-gctctagattaatg-gtgatgatggt gatgatcgacaaaatcaccg-3' (SEQ ID NO: 11) was used in substitute for the maoC primer 2. Furthermore, the PCR fragment was inserted into a pTac99A vector containing a tac promoter digested with SacI/XbaI, thereby recombinant vector pTac99MaoCH was constructed (see, FIG. 4). The pTac99A vector was constructed by digesting a pKK223-3 vector (Pharmacia Biotech. Co., Uppsala, Sweden) with PvuII/EcoRI to give the tac promoter, and cloning the tac promoter into pTrc99A (Pharmacia Biotech. Co., Uppsala, Sweden) digested with PvuII/EcoRI. FIG. 4 is a gene map of the recombinant vector pTac99MaoCH containing the maoC gene. *E. coli* DH5α was transformed with the recombinant vector pTac99MaoCH to produce recombinant *E. coli* DH5α (pTac99MaoCH). The *E. coli* strain DH5α was cultured in LB medium for one day, and added with 1 mM IPTG to induce protein expression. The colony was collected, homogenized and applied on a NTA column (Qiagen Ni-NTA kit, USA) to obtain a purified MaoC protein containing 6 histidines.

The purified MaoC protein and 0.25 mM crotonyl-CoA as a substrate were added to and mixed with reaction buffer (50 mM Tris-HCl, pH 8.0), and enoyl-CoA hydratase activity was measured by following a reduction in absorbance at 263 nm due to the hydration of crotonyl-CoA. In this case, the $\epsilon_{263}$ of enoyl-CoA thioester as a product was calculated at 6700 M$^{-1}$cm$^{-1}$. As a result, it could be found that the MaoC protein showed the activity of enoyl-CoA hydratase of 47.6 U/mg toward crotonyl-CoA.

INDUSTRIAL APPLICABILITY

As described and proved above, when the maoC gene whose function has not been yet fully established is used according to the present invention, high quality PHA with a higher number of carbon atoms than the prior PHA can be produced at a higher efficiency. Thus, the present invention will be widely applied in the production of high quality PHA.

Furthermore, the E. coli WB101 showed the highest PHA production, and MCL-PHA could be produced by amplification of the maoC gene and the PHA synthase gene in the recombinant E. coli W3110 (control group) having the normal pathway for fatty acid degradation, although the synthesis of PHA was possible by the use of the maoC gene alone. Considering that PHA cannot be generally produced from a fatty acid as a carbon source in fed-batch culture using fadB gene-deleted E. coli, the inventive method for producing MCL-PHA through amplification of the maoC gene in recombinant E. coli having the normal pathway for fatty acid degradation can be applied for the mass production of MCL-PHA by fed-batch culture.

---

What is claimed is:

1. An *E. coli* transformed with a recombinant vector comprising a polynucleotide encoding amino acids 1 to 681 of SEQ ID NO:1, wherein said *E. coli* lacks a functional fadB gene, and wherein said *E. coli* comprises a polyhydroxyalkanoate (PHA) synthase gene of *Pseudomonas* species.

2. The *E. coli* according to claim 1, wherein the PHA synthase gene is carried by a vector.

3. The *E. coli* according to claim 1, wherein the PHA synthase gene is phaC.

4. A method for producing middle-chain-length polyhydroxyalkanoate (MCL-PHA), which comprises:

(i) culturing the *E. coli* according to claim 1 in a medium containing a C6–10 carbon source to produce MCL-PHA; and (ii) recovering MCL-PHA consisting of monomers with 6–10 carbon atoms from the *E. coli* of (i).

5. The *E. coli* according to claim 1, wherein the PHA synthase gene is integrated into a chromosome of the *E. coli*.

6. The *E. coli* according to claim 1, wherein said *E. coli* lacks a functional, endogenous maoC gene.

7. The *E. coli* according to claim 1, wherein said *E. coli* is a fadB deletion mutant.

* * * * *